United States Patent
Dhimolea et al.

(10) Patent No.: US 10,221,381 B2
(45) Date of Patent: Mar. 5, 2019

(54) SYSTEMS, APPARATUS, AND METHODS RELATED TO MAGNETICALLY-CONTROLLED THREE-DIMENSIONAL TISSUE CULTURES

(71) Applicant: Dana-Farber Cancer Institute, Inc., Boston, MA (US)

(72) Inventors: Eugen Dhimolea, Malden, MA (US); Constantine Mitsiades, Boston, MA (US)

(73) Assignee: Dana-Faber Cancer Institute, Inc., Boston, MA (US)

(*) Notice: Subject to any disclaimer, the term of this patent is extended or adjusted under 35 U.S.C. 154(b) by 0 days.

(21) Appl. No.: 15/320,716

(22) PCT Filed: Jun. 30, 2015

(86) PCT No.: PCT/US2015/038510
§ 371 (c)(1),
(2) Date: Dec. 20, 2016

(87) PCT Pub. No.: WO2016/004015
PCT Pub. Date: Jan. 7, 2016

(65) Prior Publication Data
US 2017/0137766 A1 May 18, 2017

Related U.S. Application Data

(60) Provisional application No. 62/019,334, filed on Jun. 30, 2014.

(51) Int. Cl.
*C12M 3/00* (2006.01)
*C12M 1/32* (2006.01)
(Continued)

(52) U.S. Cl.
CPC ............ *C12M 23/12* (2013.01); *C12M 21/08* (2013.01); *C12M 23/06* (2013.01); *C12M 25/04* (2013.01); *C12M 25/14* (2013.01); *C12M 29/10* (2013.01)

(58) Field of Classification Search
CPC ...... C12M 21/08; C12M 23/06; C12M 23/12; C12M 25/04; C12M 29/10; C12M 35/06
See application file for complete search history.

(56) References Cited

U.S. PATENT DOCUMENTS

2009/0220979 A1* 9/2009 Davis ............... G01N 33/54333
435/6.13
2013/0260364 A1 10/2013 Zhang

FOREIGN PATENT DOCUMENTS

WO     WO 89/07880 A2    9/1989
WO     WO 03/022985 A2    3/2003
(Continued)

OTHER PUBLICATIONS

Souza et al. "Three-dimensional tissue culture based on magnetic cell levitation." Letter: Nature Nanotechnology, vol. 5 (Apr. 2010), pp. 291-296. (Year: 2010).*

(Continued)

*Primary Examiner* — William H. Beisner
(74) *Attorney, Agent, or Firm* — Cooley LLP; Cynthia A. Kozakiewicz; Ivor R. Elrifi

(57) ABSTRACT

Systems, devices, and methods for generating, culturing, and using magnetically-controlled three-dimensional (3D) tissues are described. A magnetically-enabled transwell system for immobilizing and supplying perfusion to a 3D mini-tissue includes a cell culture vessel with at least a first chamber and a second chamber, the mini-tissue being disposed in the first chamber, and a perfusion mechanism defining an elongate perfusion channel with a proximal end in the first chamber and a distal end in fluid communication (Continued)

with the second chamber, with a magnetic element configured to immobilize a magnetically-controlled 3D mini-tissue such that the proximal end is in fluid communication with basolateral space of the immobilized mini-tissue.

20 Claims, 6 Drawing Sheets

(51) Int. Cl.
*C12M 1/12* (2006.01)
*C12M 1/00* (2006.01)

(56) References Cited

FOREIGN PATENT DOCUMENTS

| WO | WO 2005/010162 A2 | 2/2005 |
| WO | WO 2012/105984 A1 | 8/2012 |
| WO | WO 2013/056019 A1 | 4/2013 |

OTHER PUBLICATIONS

Breslin S. et al. "Three-dimensional cell culture: the missing link in drug discovery" Drug Discovery Today, 2012, 18(5-6):240-249 (epub doi: 10.1016/j.drudis.2012.10.003, pp. 1-10 provided).

Egles C. et al. "Three-dimensional human tissue models of wounded skin", Methods Mol. Biol. 2010, 585:345-359 (Epub doi:10.1007/978-1-60761-380-0_24, pp. 1-12 provided).

* cited by examiner

SYSTEMS, APPARATUS, AND METHODS RELATED TO MAGNETICALLY-CONTROLLED THREE-DIMENSIONAL TISSUE CULTURES

CROSS-REFERENCE TO RELATED APPLICATIONS

This application is a national stage of and claims the benefit under 35 U.S.C. § 371 of International Patent Application No. PCT/US15/38510, entitled "Systems, Apparatus, and Methods Related to Magnetically-Controlled Three-Dimensional Tissue Cultures," filed Jun. 30, 2015, which in turn claims a priority benefit of U.S. Provisional Patent Application No. 62/019,334, entitled "Magnetically-Controlled Three-Dimensional Tissue Cultures, Systems, and Methods of Use Thereof," filed on Jun. 30, 2014, the contents of both of which applications are incorporated herein by reference in their entirety.

TECHNICAL FIELD

The present disclosure relates generally to magnetically-controlled three-dimensional (3D) tissue cultures. More specifically, the present disclosure relates to methods, systems, and devices for generating and using magnetically-controlled 3D tissue cultures for, as an example, screening of perturbagens, including but not limited to small molecules, peptides, antibodies, RNAi/shRNA constructs, and/or any other interventive modalities of cellular, acellular, and/or environmental origin with potential efficacy in cancer and other disease states.

BACKGROUND

Two-dimensional (2D) cell cultures, in which cells are grown as monolayers, are routinely used as in vitro models of normal and/or diseased tissues for evaluating the effectiveness and/or safety of libraries of molecules with potential as therapeutic drugs. While this screening step precedes preclinical animal studies which are typically required before human clinical trials, cell culture assays can be determinative for initial, yet crucial, "stop/go" decisions on the development of a drug. However, the increasingly recognized role of the in vivo microenvironment in cell response to therapeutic agents and the structural complexity of the living stroma, including cellular barriers, necessitate the incorporation of additional histological and cellular components in in vitro disease models and screening assays.

Three-dimensional (3D) tissue cultures are in vitro models that mimic the architecture of normal and/or diseased tissues. While possible to co-culture with other cells and cellular components that naturally occur in their microenvironment, 3D tissue cultures have been more analogous to conventional monolayer cell cultures than to the in vivo microenvironment of the tissue being modeled.

Furthermore, the usefulness of 3D tissue cultures as in vitro models of normal and/or diseased physiological systems for high throughput screening (HTS) applications and other large-scale studies has been severely limited by technical limitations. For example, existing 3D tissue culture systems do not provide HTS-amenable perfusion of the basolateral space of a cellularized 3D matrix. Specifically, a cellularized 3D matrix in a 3D tissue culture can be coated with a layer of epithelial and/or endothelial cells developed to form a cellular barrier between the cellularized 3D matrix and the surrounding air or cell culture medium. This cellular barrier can reduce or prevent penetration of essential nutrients into the cellularized 3D matrix of the 3D tissue culture and/or exit of toxic metabolic byproducts and waste out of the cellularized 3D matrix of the 3D tissue culture. As a result, the viability of the cells growing in the cellularized 3D matrix is reduced, thus limiting the useful duration time of the 3D tissue culture. One limited solution to this perfusion problem is the use of a transwell system.

FIGS. 1A and 1B illustrate a conventional transwell system supporting a 3D tissue culture. The transwell system includes a transwell vessel 100 with an upper chamber 102 and a lower chamber 104, defined and separated by a semi-permeable membrane 106 that allows perfusion between the chambers. In FIG. 1A, a cellularized 3D matrix 108 is cast in the upper chamber 102 of the transwell and perfused with cell culture medium from the lower chamber 104 via the semi-permeable membrane 106 to begin a 3D tissue culture. A layer of, for example, epithelial or endothelial cells coats the cellularized 3D matrix 108 to form a cellular barrier/interface 110 between the cellularized 3D matrix 108 and air or other media in the upper chamber 102.

In FIG. 1B, the cellularized 3D matrix 108 has contracted in the upper chamber 102 of the transwell vessel 100 to form a contracted 3d matrix 112 that maintains the cellular barrier/interface 110. The majority of 3D tissue cultures involve the use of contractile matrices (e.g., collagen-based gels) and/or matrix-contracting cells (e.g., fibroblasts) that can lead to contraction of a cellularized 3D matrix. Matrix contraction is also a physiological requirement for the in vitro differentiation of some tissue models (e.g., skin). Importantly, this contraction of cellularized 3D matrices during the course of a 3D tissue culture is not only common but also can result in partial or complete detachment of a cellularized 3D matrix from the semi-permeable membrane between the upper chamber and the lower chamber of a transwell vessel, thereby preventing cellular barrier-mediated phase separation (e.g., an air-liquid or liquid-liquid interface).

FIG. 1B shows that detachment of the cellularized 3D matrix 108 (contracted as a result of cell-induced matrix contraction) from the semi-permeable membrane 106 allows the medium in the lower chamber 104 to flood the upper chamber 102. This, in turn, leads to mixture of the two media and loss of a liquid-liquid interface (simulating an endothelial barrier or gastrointestinal epithelium) or loss of an air-liquid interface (simulating skin or lung epithelium). Regardless, the architectural integrity of the transwell system is compromised. Careful macroscopic and/or microscopic examination of each 3D tissue culture in a transwell system is necessary to establish that the functional architecture of any cellularized 3D matrices is intact and that the upper chamber is not flooded with medium from the lower chamber. This makes the use of a transwell system impractical for most HTS applications.

Scalability and compatibility with HTS instruments are also limitations for the use of existing 3D tissue cultures in drug discovery. Industrial-scale HTS efforts probe the biological activity of large chemical libraries consisting of hundreds of thousands of molecules (synthetic or natural extracts) and reagents (e.g., antibodies, peptides, shRNA/siRNA constructs, etc.). Screening protocols make use of industry-standard multi-well plates (including 12, 24, 96, 384, or 1536 wells) for testing molecules and compatible instruments for assay readouts. The generation of cellularized 3D structures in cell culture vessels often requires time-periods of several days, by when cell-extracellular matrix interactions often have already resulted in partial or complete matrix detachment of the structures from the vessel walls (e.g., floating collagen gels).

In parallel, long-term culture conditions necessitate several cycles of vacuum-aspiration of the depleted culture medium and replacement with fresh medium. In conventional 2D cultures, cells are attached to the bottom of the well and therefore automated aspiration of medium from multi-well plates (using multi-channel vacuuming devices) without disrupting the cells is typically feasible. In contrast, 3D tissue cultures are often miniaturized modules of cellularized matrix floating freely within a cell culture vessel. Therefore, aspiration of the medium from a 3D tissue culture vessel has a high probability of causing cellularized 3D matrix loss by aspiration, cellularized 3D matrix damage/fractionation, and/or blockage of a vacuuming channel. These artifactual events can induce major interference with the output of an assay, thus rendering this technical hurdle a major impasse for most efforts to automate HTS efforts with 3D tissue cultures.

Additionally, assay readouts of 3D tissue culture use macroscopic or microscope examination to analyze the structure and/or size of cellularized 3D structures formed within the culture. However, the random positions of floating cellularized 3D structures make 3D tissue cultures poorly suited for automated high-content imaging techniques. Furthermore, automated transfer of cellularized 3D matrices for study is challenging to do without damage/fractionation because the matrices are typically soft and brittle structures.

Accordingly, a need exists for methods, systems, and/or devices for the production, manipulation, and/or analysis of 3D tissue cultures, particularly for HTS applications.

BRIEF SUMMARY

The present application discloses a magnetically-enabled transwell system for immobilizing and supplying perfusion to at least one 3D magnetically-controlled mini-tissue (MCMT), including a cell culture vessel with at least a first chamber and a second chamber, the at least one MCMT being disposed in the first chamber, a perfusion mechanism including at least one elongate tubular body, each elongate tubular body defining an elongate perfusion channel having a proximal end located in the first chamber and a distal end configured for fluid communication with the second chamber, each elongate tubular body comprising at least one magnetic element configured to immobilize an MCMT such that the proximal end of the elongate perfusion channel is in fluid communication with basolateral space of the immobilized MCMT. The perfusion mechanism is configured to operate to infuse a medium fluid from the second chamber through at least one elongate perfusion channel into the basolateral space of at least one immobilized MCMT and/or effuse a waste fluid from the basolateral space of at least one immobilized MCMT through at least one elongate perfusion channel into the second chamber.

In one embodiment, the at least one magnetic element comprises a ferromagnetic material. The at least one magnetic element may be the elongate tubular body itself, substantially composed of a ferromagnetic material. The at least one magnetic element may be at least one of incorporated in and attached to the elongate tubular body at a position located at least one of along the elongate perfusion channel defined by the elongate tubular body and substantially near the distal end of the elongate perfusion channel defined by the elongate tubular body. The at least one magnetic element may be a ring positioned to surround the elongate tubular body substantially near the distal end of the elongate perfusion channel.

In one embodiment, the at least one MCMT is at least partially coated with at least one of endothelial cells, epithelial cells, and an acellular material. The endothelial cells may be of at least one of vascular origin and lymphatic origin. The epithelial cells may be of at least one of skin origin, lung origin, upper respiratory tract origin, kidney origin, genitourinary origin, gastrointestinal origin, endocrine origin, and exocrine origin. The epithelial cells may be derived from at least one of an eye or its components and an ear or its components. The acellular material may be at least one of an organic material and an inorganic material.

In one embodiment, the system is configured to simulate a perfused air-liquid interface or a perfused liquid-liquid interface. The perfusion mechanism may be configured to infuse medium fluid from the second chamber through at least one elongate perfusion channel into the basolateral space of at least one MCMT by capillary fluid movement, communicating vessels, a differential atmospheric pressure between the first chamber and the second chamber, and/or a differential hydrostatic pressure between the first chamber and the second chamber. The medium fluid may be a cell growth medium. Alternatively, the perfusion mechanism may be configured to effuse waste fluid from the basolateral space of at least one MCMT through at least one elongate perfusion channel into the second chamber by diffusion, gravity, periodical creation of negative hydrostatic pressure in the second chamber, periodical creation of positive hydrostatic pressure in the first chamber, periodical creation of negative atmospheric pressure in the second chamber, and/or periodical creation of positive atmospheric pressure in the first chamber.

In one embodiment, the system is configured to improve viability of the at least one MCMT to a level of viability spanning more than at least one of 1 day, 2 days, 3 days, 4 days, 5 days, and 6 days. The system may be configured to improve viability of the at least one MCMT to a level of viability spanning more than at least one of 1 week, 2 weeks, 3 weeks, 4 weeks, 5 weeks, 6 weeks, and 7 weeks. The system may be configured to improve viability of the at least one MCMT to a level of viability spanning more than at least one of 2 months, 3 months, 4 months, 5 months, 6 months, and 1 year.

The present application also discloses a method for immobilizing and supplying perfusion to at least one 3D MCMT, including a step of providing a magnetically-enabled transwell system including a cell culture vessel including at least a first chamber and a second chamber, the at least one MCMT being disposed in the first chamber, and a perfusion mechanism including at least a first elongate tubular body, the first elongate tubular body defining a first elongate perfusion channel having a proximal end located in the first chamber and a distal end configured for fluid communication with the second chamber, the first elongate tubular body comprising at least a first magnetic element. The method also includes the steps of immobilizing an MCMT with a magnetic pull force of at least the first magnetic element of at least the first elongate tubular body such that the proximal end of at least the first elongate perfusion channel is in fluid communication with basolateral space of the immobilized MCMT, and operating the perfusion mechanism to infuse a medium fluid from the second chamber through the first elongate perfusion channel into the basolateral space of the immobilized MCMT and/or effuse a waste fluid from the basolateral space of the immobilized MCMT through the first elongate perfusion channel into the second chamber.

In one embodiment, the method includes a step at least partially coating the immobilized MCMT with at least one of endothelial cells, epithelial cells, and an acellular material. The method may include a step of simulating at least one of a perfused air-liquid interface and a perfused air-liquid interface in at least one of a normal state and a disease state. The immobilized MCMT may have a level of viability spanning more than at least one of 1 day, 2 days, 3 days, 4 days, 5 days, and 6 days. The immobilized MCMT may have a level of viability spanning more than at least one of 1 week, 2 weeks, 3 weeks, 4 weeks, 5 weeks, 6 weeks, and 7 weeks. The immobilized MCMT may have a level of viability spanning more than at least one of 2 months, 3 months, 4 months, 5 months, 6 months, and 1 year.

The present application also discloses a device for immobilizing and positioning at least one 3D MCMT in a cell culture vessel, the device including an outer frame member configured to be compatible with and substantially in contact with the cell culture vessel, the cell culture vessel including at least a first well with at least one MCMT disposed within the first well, the frame member including at least a first magnetic element corresponding to the first well of the cell culture vessel such that a magnetic pull force of at least the first magnetic element at least one of immobilizes and positions the at least one MCMT disposed within the first well of the cell culture vessel.

In one embodiment, the cell culture vessel is a multi-well plate, including at least one of 1, 6, 12, 24, 96, 384, and 1536 wells. The at least one magnetic element may include a plurality of magnetic particles arranged to correspond to particular wells in at least one of a row and a column of wells in the multi-well plate. At least one magnetic element may be further arranged to correspond to a particular location in the particular well of the vessel and configured such that the magnetic pull force of the at least one magnetic element at least one of immobilizes and positions the at least one MCMT disposed in the particular well of the vessel at the particular location. In one embodiment, the magnetic pull force of the at least one magnetic element levitates the at least one MCMT.

In one embodiment, the device is configured to at least one of immobilize and position at least one MCMT during medium aspiration, medium replenishment, transfer of the at least one MCMT, long-term culture of the at least one MCMT, freezing of the at least one MCMT, defrosting of the at least one MCMT, imaging analysis of the at least one MCMT, and/or an assay procedure.

The present application also discloses a method for immobilizing and positioning at least one 3D MCMT in a cell culture vessel, the method including contacting the cell culture vessel with an outer frame member, the cell culture vessel including at least a first well with at least one MCMT disposed within the first well, the frame member including at least a first magnetic element corresponding to the first well of the cell culture vessel, such that a magnetic pull force of at least the first magnetic element at least one of immobilizes and positions the at least one MCMT disposed within the first well of the cell culture vessel.

In one embodiment, the method further includes, after at least one of positioning and immobilizing the at least one MCMT, aspirating any cell culture medium, replenishing any cell culture medium, transferring at least one MCMT, culturing at least one MCMT for one day or longer, freezing at least one MCMT, defrosting at least one MCMT, imaging at least one MCMT, and/or performing an assay procedure.

The present application also discloses a system for loading at least one of a magnetic particle and a 3D MCMT into a cell culture vessel, the system including a loading frame member configured to be compatible with and substantially in contact with the cell culture vessel, the vessel comprising at least one well, the loading frame member magnetically carrying at least one of a magnetic particle and an MCMT, each of the at least one of a magnetic particle and MCMT arranged on the loading frame member to correspond to a particular well of the vessel, the loading frame member being configured to insert the at least one of a magnetic particle and an MCMT into the at least one corresponding well of the vessel and detach from the at least one of a magnetic particle and an MCMT.

In one embodiment, the loading frame member is magnetically carrying at least one magnetic particle, the at least one magnetic particle having an elongated shape such that it can be inserted into the at least one corresponding well of the vessel. The loading frame member may exert a magnetic pull force on each of the at least one of a magnetic particle and an MCMT that is larger than a first gravitational force exerted on one of at least one of a magnetic particle and an MCMT but smaller than a second gravitational force exerted on two of at least one of a magnetic particle and an MCMT. At least a portion of the loading frame member may have magnetic properties that are permanent, inducible, and/or transient.

The system may also include an outer frame member configured to be compatible with and substantially in contact with the cell culture vessel opposite the loading frame member, the outer frame member including at least one magnetic element, wherein the at least one magnetic element of the outer frame member is arranged to correspond to a particular well of the vessel and configured such that a first magnetic pull force exerted by the at least one magnetic element of the outer frame member on the at least one of a magnetic particle and an MCMT is larger than a second magnetic pull force exerted by the loading frame member on the at least one of a magnetic particle and an MCMT.

The present application also discloses a method for loading at least one of a magnetic particle and a 3D MCMT into a cell culture vessel, the method including contacting the cell culture vessel with a loading frame member, the cell culture vessel including at least a first well, the loading frame member magnetically carrying at least one of a first magnetic particle and a first MCMT, the at least one of a first magnetic particle and a first MCMT corresponding to the first well of the cell culture vessel. The method also includes inserting the at least one of a first magnetic particle and a first MCMT into the first well of the cell culture vessel, and detaching the at least one of a first magnetic particle and a first MCMT from the loading frame member.

In one embodiment, the also includes, after loading at least one of a magnetic particle and an MCMT, deploying at least one magnetic particle, aspirating any cell culture medium, replenishing any cell culture medium, transferring at least one MCMT, culturing at least one MCMT for one day or longer, freezing at least one MCMT, defrosting at least one MCMT, imaging at least one MCMT, and/or performing an assay procedure.

The present application also discloses a 3D magnetically-controlled mini-tissue (MCMT), including an extracellular matrix, at least one cell of interest, and at least one magnetic particle enmeshed within the matrix by at least one of mechanical attachment and chemical attachment such that the position of the MCMT is precisely and adjustably controllable.

In one embodiment, the at least one magnetic particle comprises a ferromagnetic material. The at least one magnetic particle may have at least one of a concaved shape, an uneven surface, and at least one hole to improve enmeshment within the matrix. The at least one magnetic particle may be at least partially coated with at least one of a molecule and a cell to improve enmeshment within the matrix. The at least one magnetic particle may define an internal cavity to improve suspension within the matrix.

In one embodiment, the extracellular matrix is sized to fit into a well of a standard multi-well plate, including at least one of 1, 6, 12, 24, 96, 384, and 1536 wells. The MCMT may have a first level of viability, such that the MCMT is configured to be stored frozen, defrosted, and reconstituted in culture, the reconstituted MCMT having a second level of viability substantially similar to the first level of viability. The MCMT may have a level of viability spanning more than at least one of 1 day, 2 days, 3 days, 4 days, 5 days, and 6 days. The MCMT may have a level of viability spanning more than at least one of 1 week, 2 weeks, 3 weeks, 4 weeks, 5 weeks, 6 weeks, and 7 weeks. The MCMT may have a level of viability spanning more than at least one of 2 months, 3 months, 4 months, 5 months, 6 months, and 1 year. The MCMT may be configured as a surrogate for screening a potential carcinogen.

The present application also discloses a 3D mini-tissue, including an extracellular matrix, sized to fit into a well of a standard multi-well plate, and at least one cell of interest, the 3D mini-tissue having a first level of viability, such that the 3D mini-tissue is configured to be stored frozen, defrosted, and reconstituted in culture in the well of a standard multi-well plate, the reconstituted 3D mini-tissue having a second level of viability substantially similar to the first level of viability. In one embodiment, the 3D mini-tissue has a first and second level of viability, each spanning more than at least one of 1 day, 2 days, 3 days, 4 days, 5 days, and 6 days. The 3D mini-tissue may have a first and second level of viability, each spanning more than at least one of 1 week, 2 weeks, 3 weeks, 4 weeks, 5 weeks, 6 weeks, and 7 weeks. The 3D mini-tissue may have a first and second level of viability, each spanning more than at least one of 2 months, 3 months, 4 months, 5 months, 6 months, and 1 year. The 3D mini-tissue may be configured as a surrogate for screening a potential carcinogen.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present invention, and be protected by the accompanying claims.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

Figure 1:
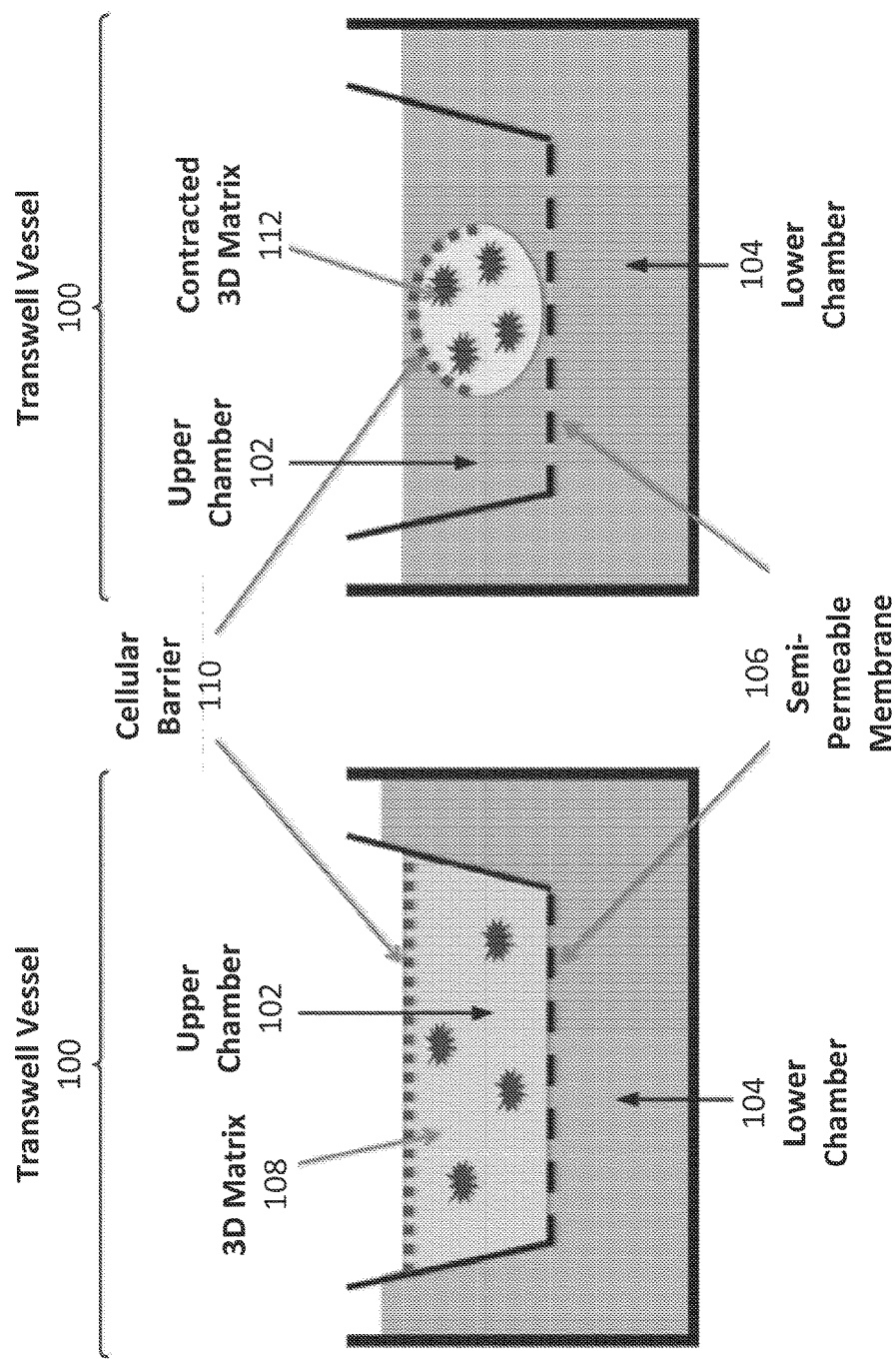
FIG. 1A illustrates a transwell system with a cellularized 3D matrix.
FIG. 1B illustrates a transwell system with a contracted cellularized 3D matrix.

The production, manipulation, and/or analysis of magnetically-controlled mini-tissues (MCMTs), as disclosed herein in accordance with some embodiments, can alleviate, circumvent, and/or overcome at least some of the technical limitations associated with existing 3D tissue cultures discussed above; particularly those challenges associated with HTS applications. In some embodiments, MCMTs are used as in vitro surrogates or models of normal and/or diseased physiological systems to simulate, for example, the growth dynamics and interactions present in tissues under normal and/or disease conditions (e.g., a malignant neoplasm and its interactions with the surrounding stroma). According to some embodiments, MCMT-based methods, systems, and/or devices can achieve, for example, fast and accurate cell culture medium aspiration and replenishment, improved transfer and long-term viability of 3D tissue cultures, freezing and defrosting of 3D tissue cultures, and automated imaging and analysis of 3D tissue cultures. According to further embodiments, these MCMT-based methods, systems, and/or devices can be modified and developed into industrial-scale processes, systems, and/or devices to, for example, generate in vitro tissue surrogates in a multi-well plate format that can be routinely used for HTS applications in the biopharmaceutical industry.

In accordance with some embodiments, MCMTs are 3D tissue cultures comprised of an extracellular matrix or scaffold, at least one cell of interest, and at least one magnetic particle (i.e., at least one particle composed of, incorporated with, and/or attached to a material with magnetic properties, such as a particle made of and/or coated with a ferromagnetic material) embedded within the matrix and enmeshed into it by mechanical and/or chemical attachment. The extracellular matrix may be natural, artificial, or a combination thereof. Natural extracellular matrices can include but are not limited to, for example, one or more of collagen, composite secretion from Engelbreth-Holm-Swarm (EHS) mouse sarcoma cells (Matrigel®, available from Corning Inc. (Tewksbury, Mass.)), fibronectin, hyaluronic, etc. Artificial extracellular matrices can include but are not limited to, for example, one or more of self-assembling peptides, silk, etc.

An MCMT is designed to include at least one magnetic particle embedded within the extracellular matrix and enmeshed into the matrix by mechanical and/or chemical attachment. Specifically, one or more magnetic particles may be immersed in the matrix while the matrix is in a liquid or semi-liquid/viscous state (i.e., before gelification). A particle may contain surface cavities or holes that allow entrapment of the particle within the matrix; after matrix gelification the enmeshed matrix functions as mechanical grip that holds the 3D culture and one or more magnetic particles together. Unlike 3D multicellular structures formed by magnetic levitation, in which antibody-coated or collagen-coated magnetic nanoparticles are delivered to individual cells in order to magnetically levitate and thereby aggregate cells in the absence of any surface or matrix (e.g., BioAssembler™, available from Nano3D Biosciences (Houston, Tex.)), an MCMT uses an extracellular matrix to provide structural and biochemical support to at least one magnetic particle and also one or more cells of interest. Because the at least one magnetic particle is embedded within the MCMT matrix and not within individual cells, the at least one magnetic particle enables precise and adjustable control of the specific positioning of the entire MCMT, thus allowing for critical and/or desirable cell culture functions without altering the MCMT structure.

In some embodiments, a magnetic particle comprises at least one particle composed of, incorporated with, and/or attached to one or more materials with magnetic properties, including but not limited to ferromagnetic materials. For example, various metals may be used to convey ferromagnetic properties, including but not limited to nickel, cobalt, and iron. Other magnetic materials may include alloys and other chemical compounds, such as stainless steel, cobalt alloys, and iron oxide. Magnetic particles may have various shapes, sizes, and types of magnetization (e.g., paramagnetic, ferromagnetic, ferromagnetic, and superparamagnetic). In some embodiments, a magnetic particle has a concaved shape and/or an uneven surface to improve attachment to the matrix. Furthermore, a magnetic particle may be coated with one or more organic and/or inorganic molecules (e.g., fibronectin, collagen, antibodies, and/or peptides that bind to matrix components) for biocompatibility and/or to generate chemical attachments to the matrix that improve the mechanical grip that holds the 3D culture and one or more magnetic particles together. A magnetic particle may also be coated with cells that attach to the matrix for improved mechanical grip. In some embodiments, a magnetic particle has one or more internal holes or cavities to improve attachment to and/or suspension within an extracellular matrix of an MCMT.

In accordance with some embodiments, MCMTs comprise one or more cells of interest from, for example, breast, lung, gastrointestinal, kidney, and/or other tissue, and/or various types of diseased tissue such as cancerous tissue. In some applications, these MCMTs are used as in vitro surrogates or models of normal and/or diseased tissues and/or physiological systems (e.g. endocrine or exocrine epithelia).

In further embodiments, the external surface of the cellularized matrix of an MCMT is partially or completely coated with a cellular barrier and/or an acellular barrier. This barrier may include one or more layers of cellular and/or acellular materials. A cellular layer may include, but is not limited to, epithelial cells and/or endothelial cells. Epithelial cells may have one or more origins including, but not limited to, skin, lung, gastrointestinal, endocrine, and exocrine tissue. Endothelial cells also may have one or more origins including, but not limited to, vascular and lymphatic tissue. In some exemplary applications, a partially- or completely-coated MCMT may be used as an in vitro surrogate or model of a normal and/or diseased physiological cellular barrier with, for example, an air-liquid interface (simulating, e.g., skin or lung epithelia) or, in a culture medium, a liquid-liquid interface (simulating, e.g., endothelial barriers in normal or neoplastic tissues, blood-brain barriers, etc.).

An acellular layer may include, but is not limited to, organic materials, inorganic materials, or combinations thereof. For example, an acellular layer may include antibodies, enzymes, proteoglycans, fibrous proteins (e.g., collagens and elastins) and other natural polymers (e.g., gelatins, silk, fibronectin, laminin, entactin, and polysaccharides), and/or other components of an extracellular matrix. In addition or alternatively, an acellular layer may include metals (e.g., lathanides and various alloys), ceramics (e.g., aluminum oxides, zirconia, and calcium phosphates), polymers (e.g., silicones, poly (ethylene), poly (vinyl chloride), polyurethanes, and polylactides), modified graphene, and/or other elastic and/or biocompatible materials.

Examples of MCMT applications include but are not limited to (i) antineoplastic drug screening using MCMTs including 3D cancer spheroids in accordance with some embodiments; (ii) HTS of molecules that perturb the function of endocrine and exocrine glands using MCMTs including epithelial glandular-like acini in accordance with some embodiments; (iii) measuring penetration of molecules, molecule-carriers, and/or cellular entities (e.g., natural killer cells and/or other endogenous or engineered immune effector cells) through epithelial barriers (e.g., the lining of the gastrointestinal tract, alveolar surfaces of the lung, etc.) using MCMTs with a coating of epithelial cells in accordance with some embodiments; and (iv) measuring penetration of compounds or compound-carriers or cellular entities (such as natural killer cells, or other endogenous or engineered immune effector cells) through endothelial barriers (e.g., the blood-brain barrier, blood-testis barrier, etc.) using MCMTs with a coating of endothelial cells.

Figure 2:
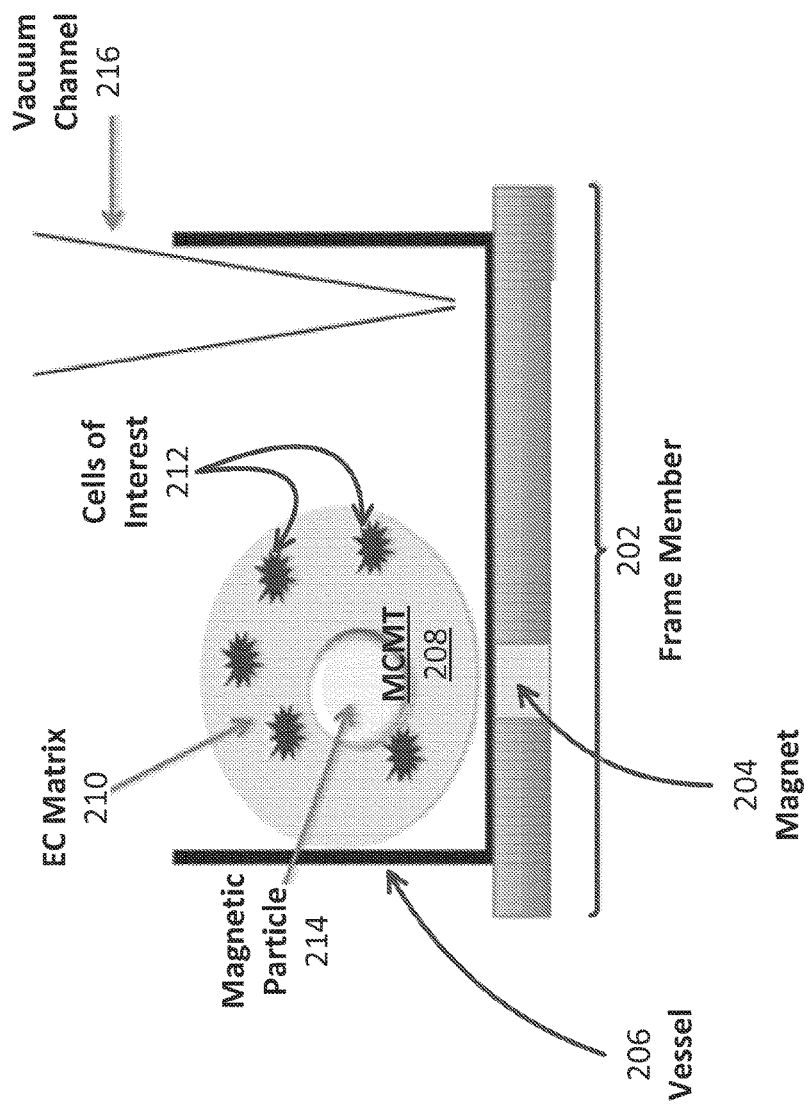
FIG. 2 illustrates a system for magnetically-adjustable positioning and/or immobilization of a 3D magnetically-controlled mini-tissue (MCMT) in accordance with some embodiments.

FIG. 2 illustrates a device and/or system for magnetically-adjustable immobilization and positioning of at least one MCMT in accordance with some embodiments. The system is configured to magnetically immobilize and/or adjust the position of an MCMT in a cell culture vessel (e.g., a petri dish, multi-well plate of 1, 6, 12, 24, 96, 384, or 1536 wells, etc.) by using a magnet-carrying device positioned outside the vessel. In some embodiments, this magnet-carrying device is an outer frame member. In some embodiment, magnet-carrying device or outer frame member is substantially composed of at least one of metal, plastic, or another material. A magnet-carrying device or outer frame member includes at least one magnet, which may be a magnetic particle, such as a ferromagnetic particle.

In some embodiments, a magnet-carrying device or outer frame member is configured to be compatible with a cell culture vessel, for example, having similar dimensions to the vessel. In some embodiments, a magnet-carrying device or outer frame member is positioned near and/or in contact with and/or removably attached to a cell culture vessel, for example, below the vessel or above a lid on the vessel. In further embodiments, the magnet-carrying device or outer frame member is positioned such that the at least one magnet is near and/or in contact with the cell culture vessel such that the magnetic pull force of the at least one magnet can immobilize and/or control the position of an MCMT disposed in the cell culture vessel. The at least one magnet may be positioned at a particular location relative to a well of the cell culture vessel, for example, at or near the bottom of the well, such that the magnetic pull force of the at least one magnet can immobilize and/or reposition an MCMT in the well at or near the particular location. In some embodiments, a magnet-carrying device or outer frame member includes more than one magnet arranged for stronger immobilization of an MCMT in a well.

For example, FIG. 2 shows a magnet-carrying device or outer frame member 202 with a magnet 204. The device or frame member 202 is positioned beneath a cell culture vessel 206 such that the magnet 204 is located near the bottom and to the left of center of a well of the vessel as shown. In FIG. 2, an MCMT 208 is disposed in the well of the cell culture vessel 206. The MCMT 208 includes an extracellular matrix 210, several cells of interest 212, and a magnetic particle 214 embedded within the matrix and enmeshed into it by mechanical or chemical attachment. The MCMT 208 has been positioned and/or immobilized at the bottom and to the left of center of the well due to the magnetic pull force of the magnet 204 attracting the magnetic particle 214.

According to some embodiments, a magnet-carrying device or outer frame member is configured to be compatible with a cell culture vessel that is a multi-well plate. In further embodiments, the magnet-carrying device or outer frame member includes a plurality of magnets or magnetic elements arranged such that each or some of the magnets or magnetic elements correspond to a well in the multi-well plate and/or each or some of the magnets or magnetic elements are positioned at or near a particular location relative to each well of the multi-well plate. The particular location may be determined such that the magnetic pull force of each magnet can immobilize and/or reposition any MCMTs in the wells at or near the particular location relative to each well of the multi-well plate. In some embodiments, the magnets are arranged to correspond to a row of wells, a column of wells, and/or another configuration of wells in the multi-well plate. In some embodiments, more than one magnet or magnetic element is arranged to correspond to one well for at least one well in a multi-well plate for stronger immobilization of any MCMTs in the at least one well.

The magnets or magnetic elements may be composed of, incorporated with, and/or attached to one or more materials with magnetic properties, including but not limited to ferromagnetic materials. For example, various metals may be used to convey ferromagnetic properties, including but not limited to nickel, cobalt, and iron. Other magnetic materials may include alloys and other chemical compounds, such as stainless steel, cobalt alloys, and iron oxide. The magnets or magnetic elements may have various shapes, sizes, and types of magnetization (e.g., paramagnetic, ferromagnetic, ferromagnetic, and superparamagnetic). Furthermore, a magnet or magnetic element may be coated with one or more organic and/or inorganic molecules for biocompatibility.

In some embodiments, a multi-well plate-compatible frame member including a number of magnets or magnetic elements arranged at positions that correspond to positions of different wells of a multi-well plate is referred to as an Outer-Multi-Magnet Frame (OMMF). Due to the arrangement of the magnets or magnetic elements embodied on the OMMF, each magnet or magnetic element corresponds to one particular well of the cell culture vessel. For example, if the OMMF is lined up under the multi-well plate, the attractive forces induced between the magnets or magnetic elements in the OMMF and the magnetic particles inside the MCMTs enable the immobilization of the MCMTs at the bottom of their respective wells. In some embodiments, different OMMFs are designed to allow the position of each magnet or magnetic element to be varied relative to the surface area of each well in order to selectively control the position of any MCMTs in the wells. In further embodiments, an OMMF is configured to selectively vary the position of each or some magnets or magnetic elements relative to the surface area of the corresponding well, thus selectively controlling the position of any MCMTs in the wells.

The positioning and/or immobilization of an MCMT at a particular location in a cell culture vessel using a magnet-carrying device or outer frame member may improve the results for, among other things, medium aspiration, medium replenishment, extraction and/or transfer of the MCMT, long-term culture of the MCMT, freezing and/or defrosting of the MCMT by allowing rapid removal of toxic cryoprotectants (e.g., DMSO), and manual and/or automated imaging and/or analysis of the MCMT in accordance with some embodiments. These advantages are particularly important for floating cell-contracted MCMTs.

As shown in FIG. 2, by positioning and/or immobilizing the MCMT 208 at the bottom and to the left side of the well, a magnet-carrying device or outer frame member 202 allows for insertion of a vacuuming channel 216 for medium aspiration on the right side of the well. The magnetic pull force of the magnet 204 attracting the magnetic particle 214 embedded and enmeshed in the MCMT 208 reduces the risk of the MCMT being aspirated by vacuuming channel 216 or otherwise damaged. Similarly, a magnet-carrying device or outer frame member may be used to position and/or immobilize an MCMT to protect it from damage caused by, for example, contact with the walls of the vessel, other channels, and/or tools, such as extraction and transfer tools.

In accordance with some embodiments, methods, systems, and devices for magnetically-adjustable immobilization and positioning of at least one MCMT, for example, the device and/or system as shown in FIG. 2 and described above, also address significant technical challenges in high-content and high-throughput screening (HTS) applications, including HTS of perturbagens, including but not limited to small molecules, peptides, antibodies, RNAi/shRNA constructs, and/or any other interventive modalities of cellular, acellular, and/or environmental origin with potential therapeutic utility. Specifically, the use of MCMTs can reduce and/or solve technical difficulties associated with one or more of medium aspiration/replenishment, long-term 3D tissue culture, and freezing/defrosting of floating 3D tissue cultures in multi-well plates.

Compared to conventional 3D tissues cultures, one particular advantage of MCMTs is the ability to maintain long-term viability (e.g., in the range of several weeks, months, or even longer) of the 3D tissue culture, which can, for example, allow enough time to (i) simulate growth dynamics of malignant neoplasms and their interactions with surrounding stroma (e.g., non-malignant cells and the extracellular matrix), and/or (ii) partially or completely coat a 3D tissue culture with cells (e.g., epithelial and/or endothelial cells) to more accurately simulate a normal and/or diseased physiological cellular barrier. Potential viability may be affected by numerous parameters, including the type(s) of cells in culture. For example, in some embodiments, an MCMT may maintain viability of a 3D tissue culture for 1, 2, 3, 4, 5, or 6 days. In further embodiments, an MCMT may maintain viability of a 3D tissue culture for 1, 2, 3, 4, 5, 6, or 7 weeks. In even further embodiments, an MCMT may maintain viability of a 3D tissue culture between 2 months to a year or even more than a year.

According to some embodiments, an MCMT-based product may be provided to an end-user as a stand-alone product. According to other embodiments, a cell-culture vessel (e.g., a petri dish, multi-well plate of 1, 6, 12, 24, 96, 384, or 1536 wells, etc.) containing at least one MCMT may be provided to an end-user. Because MCMTs are capable of being rapidly defrosted, in accordance with some embodiments, an MCMT-containing vessel may be frozen and shipped, for example, over a long distance, thus significantly increasing availability to end-users.

In accordance with some embodiments, the production of an MCMT includes the casting of a cellularized 3D matrix around at least one magnetic particle or embedding/enmeshing of at least one magnetic particle into the extracellular matrix of a cellularized 3D structure by mechanical and/or chemical attachment, thereby configuring the resulting MCMT to be controlled using an external magnetic source. According to some embodiments, methods, systems, and devices for magnetically controlled, rapid, and/or automated deployment of a magnetic particle into a cell culture vessel, as part of a workflow for the production of MCMTs, are described herein.

FIGS. 3A-3D illustrate at least a portion of an MCMT production workflow using a magnetic particle loading device and/or system in accordance with some embodiments. The system is configured to magnetically control deployment of at least one magnetic particle (or MCT) 300 into at least one well of a cell culture vessel (e.g., a petri dish, multi-well plate of 1, 6, 12, 24, 96, 384, or 1536 wells, etc.) by using a loading frame device positioned outside the vessel and referred to as a magnetic or Ferromagnetic Particle Loading Device (FPLD) 302 according to some embodiments.

In some embodiments, an FPLD is loaded with at least one magnetic particle, such as a ferromagnetic particle. Each magnetic particle may be composed of, incorporated with, and/or attached to one or more materials with magnetic properties. For example, various metals may be used to convey ferromagnetic properties, including but not limited to nickel, cobalt, and iron. Other magnetic materials may include alloys and other chemical compounds, such as stainless steel, cobalt alloys, and iron oxide. Magnetic particles may have various shapes—such as, for example, the elongated shape of the magnetic particle 300 shown in FIGS. 3A—and sizes that allow for the magnetic particle to be freely inserted within the intended cell culture vessel. Magnetic particles may also vary in type of magnetization (e.g., paramagnetic, ferromagnetic, ferromagnetic, and superparamagnetic). In some embodiments, a magnetic particle has a concaved shape and/or an uneven surface to improve attachment to an extracellular matrix of an MCMT. Furthermore, a magnetic particle may be coated with one or more organic and/or inorganic molecules (e.g., fibronectin, collagen, antibodies, and/or peptides that bind to matrix components) for biocompatibility and/or to generate chemical attachments to a matrix that improve the mechanical grip that holds the 3D culture and one or more magnetic particles together. A magnetic particle may also be coated with cells that attach to the matrix for improved mechanical grip. In some embodiments, a magnetic particle has one or more internal holes or cavities to improve attachment to and/or suspension within an extracellular matrix of an MCMT.

In some embodiments, an FPLD includes a frame member, which may be configured to be compatible with a cell culture vessel, for example, having similar dimensions to the vessel. According to some embodiments, the magnetic properties of an FPLD, or one or more portions (modules) of an FPLD, may be permanent (e.g., comprising a ferromagnetic material) and/or induced/transient (e.g., via electromagnetization). In some embodiments, the magnetic pull force exerted by an FPLD on each magnetic particle (or MCMT) is higher than the gravitational forces exerted on the magnetic particle (or a MCMT). In further embodiments, the magnetic pull force exerted by an FPLD on each magnetic particle (or MCMT) is smaller than the gravitational forces exerted on two or more magnetic particles (or MCMTs). These properties may allow one or more magnetic/magnetized modules of an FPLD to each lift/transfer one magnetic particle (or MCMT) from a container and load it into another container in accordance with some embodiments.

In some embodiments, an FPLD with permanent magnetic properties loads a magnetic particle (or MCMT) into a cell culture vessel by positioning a magnetic/magnetized module of an FPLD above the vessel opening so that the magnetic particle is freely inserted in the vessel. Then, a magnet-carrying device or outer frame member (e.g., an OMMF)—with higher magnetic pull force than the FPLD— may be positioned opposite the FPLD and under the vessel. The magnet-carrying device or outer frame member may be used to immobilize the magnetic particle (or MCMT) in the vessel such that it remains in the vessel once the FPLD is removed.

In alternative embodiments, an FPLD with induced/transient magnetic properties loads a magnetic particle (or MCMT) into a cell culture vessel by positioning the FPLD, or a module thereof, above the vessel so that the magnetic particle is freely inserted in the vessel. Then, a disruption and/or demagnetization of the FPLD can cause release of the magnetic particle (or MCMT) in the vessel such that it remains in the vessel once the FPLD is removed.

According to some embodiments, an FPLD is configured to be compatible with a cell culture vessel that is a multi-well plate. In further embodiments, the FPLD is configured to transfer each or some of a plurality of magnetic particles into corresponding wells of a multi-well plate. Thus, an FPLD can enable production of MCMTs in corresponding formats (e.g., 96- or 384-well plates). The shape of the distal end of each FPLD module may be modified such as to accommodate the size and shape of the transferred object (e.g., a ferromagnetic particle and/or an MCMT). For example, the distal end of an FPLD module may be a concaved shape with a fixed diameter such that the distal end of the FPLD module can accommodate a spherical ferromagnetic particle and/or a spherical MCMT of similar diameter.

Figure 3:
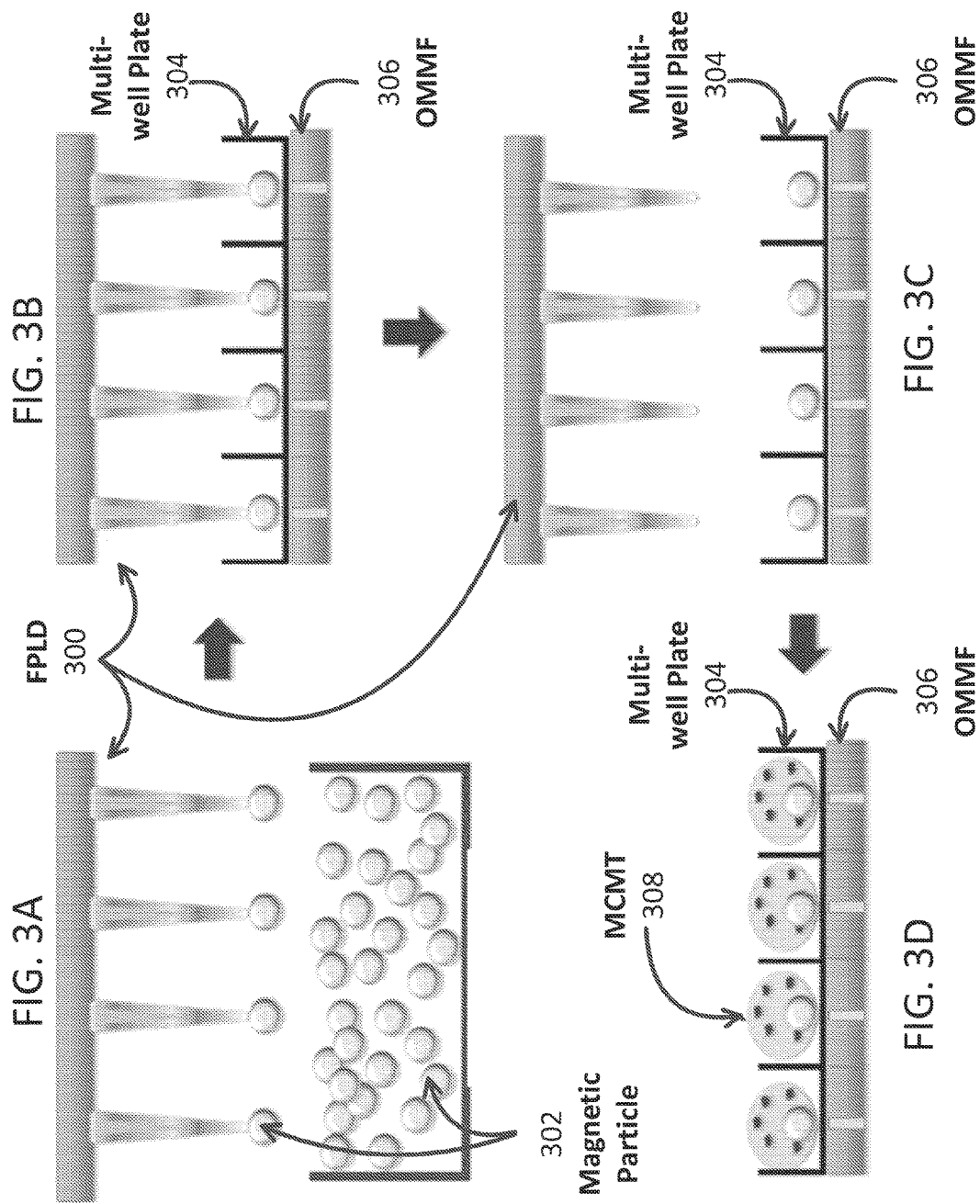
FIGS. 3A-3D illustrate an MCMT production workflow using a magnetic particle loading device and/or system in accordance with some embodiments.

For example, FIGS. 3A-3D illustrate a method of producing MCMTs using a magnetic particle loading device and/or system in accordance with some embodiments. In FIG. 3A, an FPLD 300 is positioned above a container comprising a plurality of magnetic particles 302. The magnetic pull force of each module of the FPLD 300 allows vertical levitation of a controlled number of magnetic particles 302. For example, as shown in FIG. 3A, four individual magnetic particles 302 are attracted to the FPLD 300.

In FIG. 3B, the FPLD 300 is repositioned over a multi-well plate 304, such that the four magnetic particles 302 are lined up with and freely inserted in the four corresponding wells of the multi-well plate 304. An OMMF 306, which may exert higher magnetic pull force than the FPLD 300, is positioned opposite the FPLD 300 and under the multi-well plate 304.

In FIG. 3C, the OMMF 306 immobilizes the magnetic particles 302 in their respective wells such that they remain in the multi-well plate 304 once the FPLD 300 is removed. The multi-well plate 304 is used then to cast 3D culture mix and generate an MCMT 308 in each of the four wells with each of the four magnetic particles 302 now embedded and enmeshed into the respective MCMT matrix, as shown in FIG. 3D.

In some embodiments, an FPLD is used to load MCMTs from a storage container (e.g., a cryocontainer) into the wells of a cell culture vessel (e.g., a multi-well plate), to briefly levitate MCMTs to allow for a medium change in the vessel, and/or to transfer MCMTs from the wells of one multi-well plate to the wells of another multi-well plate.

Figure 4:
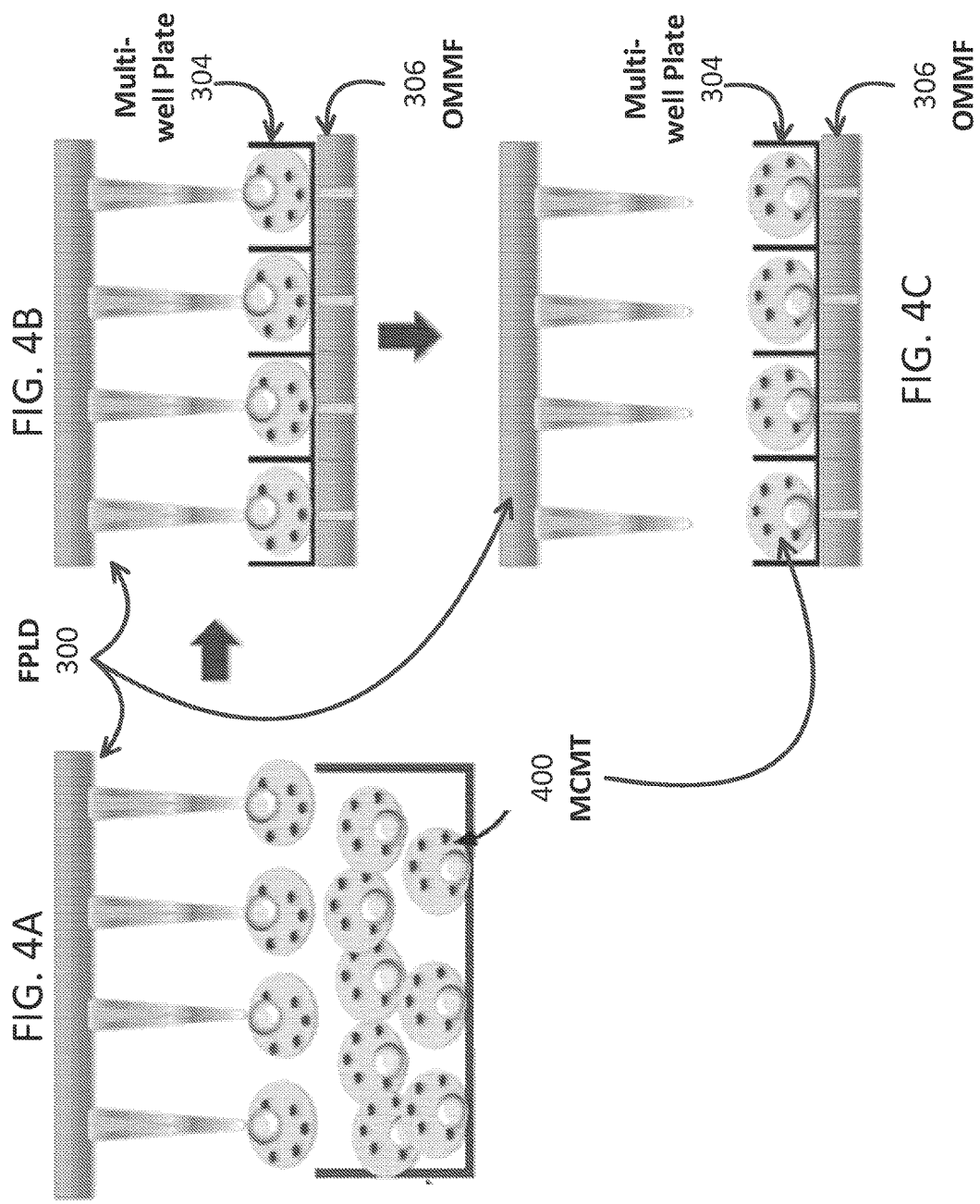
FIGS. 4A-4C illustrate a method of loading detached/floating MCMTs into a multi-well plate using a magnetic particle loading device and/or system in accordance with some embodiments.

For example, FIGS. 4A-4C illustrate a method of loading freely floating MCMTs into a multi-well plate using a magnetic particle loading device and/or system (e.g., an FPLD) in accordance with some embodiments. In FIG. 4A, an FLPD 300 is positioned above a container comprising a plurality of freely floating MCMTs 400. The magnetic pull force of each module of the FPLD 300 allows vertical levitation of a controlled number of MCMTs 400, for example, four MCMTs 400, as shown in FIG. 4A.

In FIG. 4B, the FPLD 300 is repositioned over a multi-well plate 304, such that the four MCMTs 400 are lined up with and freely inserted in the four corresponding wells of the multi-well plate 304. An OMMF 306, which may exert higher magnetic pull force than the FPLD 300, is positioned opposite the FPLD 300 and under the multi-well plate 304. The OMMF 306 immobilizes the MCMTs 400 in their respective wells such that they remain in the multi-well plate 304 once the FPLD 300 is removed, as shown in FIG. 4C. The multi-well plate 304 loaded with MCMTs 400 can now be used in any of various applications in accordance with some embodiments.

According to some embodiments, more than one MCMT is disposed and subject to manipulation and/or analysis in a cell culture vessel. For example, a plurality of MCMTs may be disposed in a petri dish or a single well of a multi-well plate. In further embodiments, each MCMT or a portion of a plurality of MCMTs is designed with different numbers and/or types of magnetic particles embedded within the extracellular matrices of the MCMTs. Different numbers and/or types of magnetic particles can respond to different magnetic pull forces. Thus, each MCMT or a portion of a plurality of MCMTs may be configured to require different magnetic pull forces. This allows for selective immobilization, positioning, and/or transfer of at least one MCMT from a plurality of MCMTs using methods, systems, and devices in accordance with some embodiments. For example, according to some embodiments, a plurality of floating MCMTs is disposed in a single well of a cell culture vessel. A first portion of the MCMTs each include a single magnetic particle while a second portion of the MCMTs each include two magnetic particles embedded in their respective matrices.

In further embodiments, a magnet-carrying device or outer frame member is positioned beneath the cell culture vessel such that a magnet is located below the well; however, the magnet is configured to have a particular magnetic pull force (e.g., a relatively weak magnetic pull force) designed to position and/or immobilize only the second portion of MCMTs. By positioning and/or immobilizing only the second portion of MCMTs at the bottom of the well, the magnet-carrying device or outer frame member allows the still-floating first portion of the MCMTs to be extracted, transferred, and/or destroyed without harming the second portion of MCMT, which are still immobilized at the bottom of the well. Tools for extraction and transfer may include, but are not limited to, a vacuuming channel and an FPLD according to some embodiments.

In alternative embodiments, an FPLD is configured to exert a particular magnetic pull force (e.g., higher than the gravitational forces exerted on each of the first portion of MCMTs, but smaller than the gravitational forces exerted on each of the second portion of MCMTs) designed to lift and/or transfer only the first portion of MCMTs. By lifting and/or transferring only the first portion of MCMTs, the FPLD allows the second portion of the MCMTs to remain in the well.

Similarly, other methods, systems, and devices may be modified such that one or more MCMTs among a plurality of MCMTs are selectively immobilized, positioned, and/or transferred in accordance with some embodiments.

Methods, systems, and/or devices for using MCMTs may be modified and developed, according to some embodiments, into industrial-scale processes and systems for producing, manipulating, and/or analyzing in vitro tissue surrogates in multi-well plates (e.g., 96- and 384-well formats), which are routinely used for HTS applications in the biopharmaceutical industry. Some embodiments allow for automated and/or simultaneous testing of experimental conditions (e.g., cell type/number, matrix composition, molecule being screened, etc.). For example, a 384-well plate can carry up to 24 different types of MCMTs. Also, the ability to freeze and thaw entire MCMT-carrying multi-well plates can significantly increase the capacity and geographic reach of, for example, a collaboration and/or commercial endeavor. Additionally, the versatility of methods, systems, and/or devices for using MCMTs, according to some embodiments, is similar to that for using conventional 2D platforms. Some embodiments are applicable to a multitude of normal (e.g., a cellular barrier) and abnormal (e.g., cancer) in vitro tissue surrogates, further increasing the number of disease settings whereby MCMT-based screenings can find HTS applications.

Other advantages of and unique opportunities associated with using MCMTs for HTS applications may include (i) early termination of screened molecules that have no clinical relevance or in vivo efficacy, thus reducing significant costs associated with inefficient further development of these molecules; (ii) discovery of novel molecules or combinations thereof that exhibit biological activity by, for example, affecting the dynamic networks of cancer-associated epithelial-mesenchymal cross-talk (e.g., intercellular and cell-extracellular membrane interactions); and (iii) better understanding of emerging features such as neoplasm morphology and differentiation grade.

Figure 5:
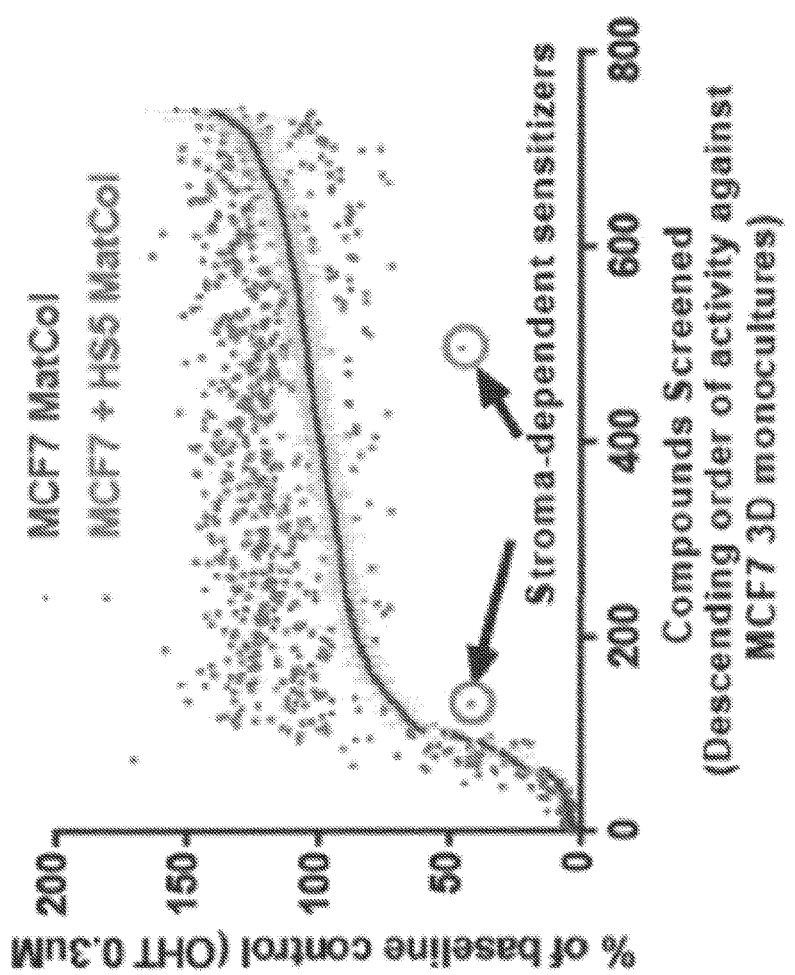
FIG. 5 is a table showing the results of a chemical library screening in accordance with some embodiments.

MCMTs-based methods, systems, and devices scaled for HTS applications, in accordance with some embodiments, may be used to test extensive libraries of bioactive molecules under numerous culture conditions. FIG. 5 is a graph illustrating a chemical library screening using panels of 3D cultures comprising mono-cultures of cells or co-cultures of cells in accordance with some embodiments. The chemical library screening was based on the NCI 60 Mechanistic Diversity Set screening, which consists of 879 compounds, derived from the 37,836 open compounds tested in the NCI human tumor 60 cell line screen to represent a broad range of structural diversity and growth inhibition patterns based on the GI50 activity of the compounds (available from the National Cancer Institute Developmental Therapeutics Program). The compounds were screened across a dose range for their ability to inhibit the growth of breast cancer cells (MCF7). The graph in FIG. 5 shows activity values in descending order of the compounds screened against (i) 3D cultures comprising mono-cultures of breast cancer cells (MCF7) and (ii) contracted 3D cultures comprising co-cultures of breast cancer cells (MCF7) and bone marrow stromal cells (HS5) using the screening system. This screening enables the identification of compounds that have increased activity against breast cancer cells in the presence of stromal cells.

In accordance with some exemplary embodiments, methods, systems, and devices for maintaining perfusion of coated MCMTs, thus enabling scalable models of cellular barriers, are described herein. The external surface of the cellularized matrix of an MCMT may be partially or completely coated with a cellular barrier, including but not limited to (i) endothelial cells for culture in a cell growth medium simulating intracapillary content; (ii) epithelial cells of skin or lung origin for culture without cell culture medium simulating the air-liquid interface; and (iii) epithelial cells of gastrointestinal or endocrine/exocrine origin to perform cell culture in appropriate cell culture medium.

Because a cellular barrier may partially or completely separate the cells within a 3D tissue culture from any surrounding fluid in the vessel, a coated MCMT may benefit from a secondary channel with access to the basolateral space (i.e., interior) of the MCMT for allowing perfusion, including the infusion of medium fluid into the basolateral space of the MCMT and/or effusion of waste fluid out of the basolateral space of the MCMT in accordance with some embodiments.

In some embodiments, a capillary-like needle defines a perfusion channel in a cell culture vessel with a proximal end protruding into the vessel and a distal end at a vessel wall. In some embodiments, a MET system is configured to enable spatial alignment of one or more perfusion channels with an MCMT in a cell culture vessel by, for example, including at least one magnetic element that positions and immobilizes the MCMT in the vessel. For example, a magnetic element may be the needle itself, or one or more portions thereof, due to permanent (e.g., composed of a ferromagnetic material) and/or induced/transient (e.g., via electromagnetization) magnetic properties of the material(s) that comprise the needle. In another example, a magnetic element (e.g., a magnetic ring) is incorporated and/or attached to the needle at a position along its shaft or at its distal end). According to some embodiments, an MCMT is positioned and immobilized such that at least a portion of the proximal end of the needle is positioned within the basolateral space of the MCMT and the perfusion channel is in fluid communication with the basolateral space of the MCMT.

Figures 6A, 6B:
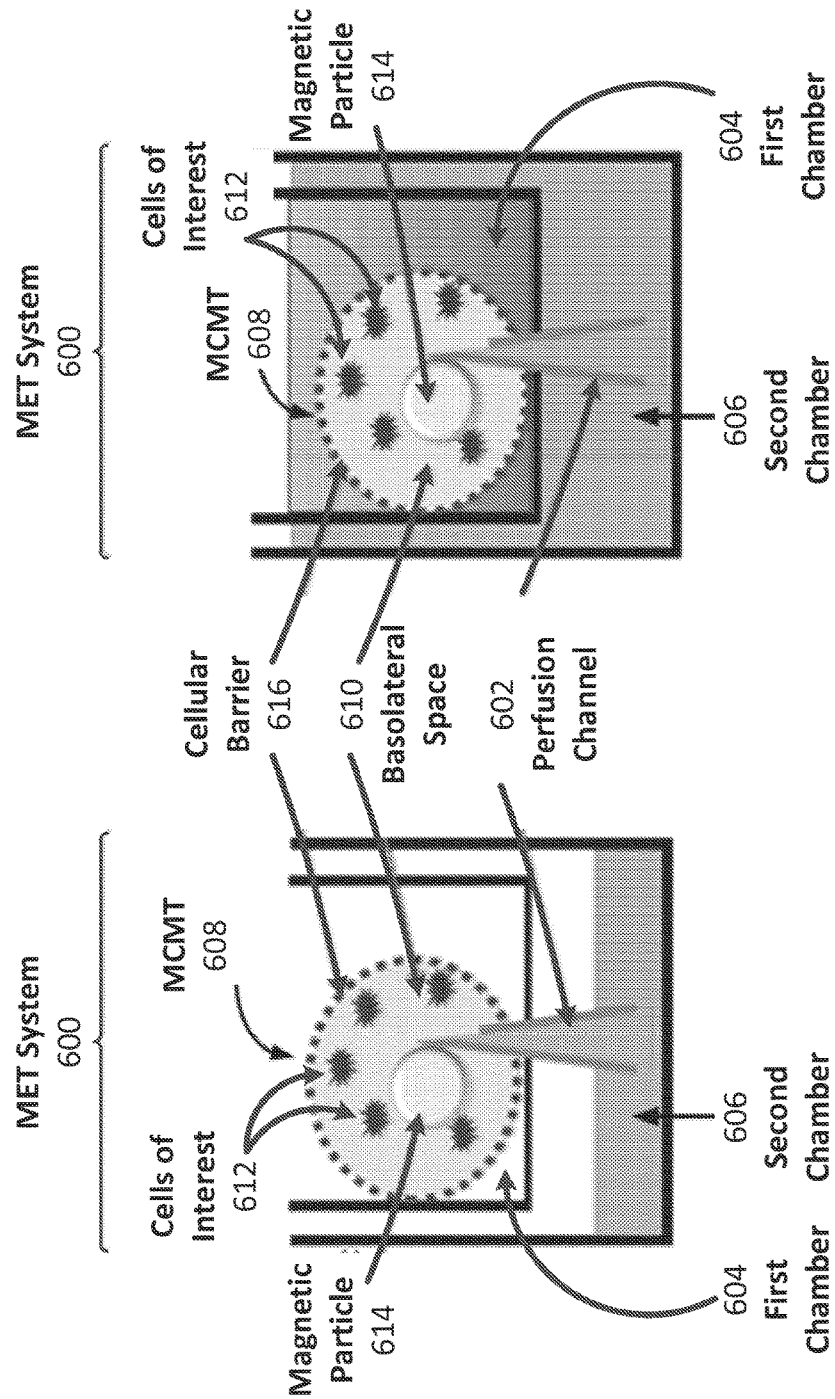
FIG. 6A illustrates a magnetically-enabled transwell (MET) system with an air-liquid interface in accordance with some embodiments.
FIG. 6B illustrates the MET system with a liquid-liquid interface in accordance with some embodiments.

For example, FIGS. 6A and 6B illustrate a magnetically-enabled transwell (MET) system 600 including at least one such perfusion channel 602 in accordance with some embodiments. In FIG. 6A, the MET system 600 simulates an air-liquid interface using a cell culture vessel with a first chamber 604 comprising air and a second chamber 606 comprising a liquid (e.g., cell growth medium). An MCMT 608 is disposed in the first chamber 604. The MCMT 608 includes an extracellular matrix 610, cells of interest 612, a magnetic particle 614 embedded within and enmeshed into the matrix 610, and a cellular barrier 614 (e.g., a coating of epithelial and/or endothelial cells). A needle defines a perfusion channel 602 with a proximal end located in the first chamber 604 and a distal end in fluid communication with the second chamber 606. The needle/perfusion channel 602 comprises a magnetic element configured to immobilize the MCMT 608 such that at least a portion of the proximal end of the needle/perfusion channel 602 is positioned past the cellular barrier 616 and within the basolateral space of the matrix 610.

In accordance with some embodiments, a perfusion mechanism enables infusion of liquid (e.g., cell growth medium) from the second chamber 606 through the needle/perfusion channel 602 into the basolateral space of the matrix 610, thus providing nutrition to the cells of interest 612. The perfusion mechanism may include but is not limited to (i) capillary liquid movement; (ii) communicating vessels; and/or (iii) a differential atmospheric pressure between the two chambers.

In FIG. 6B, the MET system 600 simulates a liquid-liquid interface using a cell culture vessel with the first chamber 604 comprising a first liquid (e.g., waste products) and the second chamber 606 comprising a second, different liquid (e.g., cell culture medium).

In accordance with some embodiments, a perfusion mechanism enables effusion of liquid (e.g., waste products) from the basolateral space of the matrix 610 of an MCMT 608 through the needle/perfusion channel 602 into the second chamber 606, thus removing toxic waste accumulated by the cellular metabolism inside the MCMT 608 and allowing for fresh cell culture medium to diffuse from the first chamber 604 through the cellular barrier 616 into the matrix 610 and reach the cells of interest 612. The perfusion mechanism may include but is not limited to (i) diffusion; (ii) gravity; (iii) creating periodical negative atmospheric pressure in the second chamber 606; and/or (iv) creating periodical positive atmospheric pressure in the first chamber 604.

According to some embodiments, MET methods and systems allow for the generation of perfused scalable models of endothelial barriers (e.g., neoplasm vasculature, blood-brain barrier, etc.), epithelial barriers (e.g., gastrointestinal epithelium, etc.), epithelial air-liquid barriers (e.g., lung and skin epithelium, etc.), and glandular/secretory epithelium (e.g., pancreatic, mammary, salivary, etc.). According to some embodiments, a broad range of HTS applications benefit from combining the scalability of MCMTs with MET functions, including but not limited to (i) in vitro experimental systems to study trans-epithelial and trans-endothelial transport of various drugs/molecules in normal and/or diseased tissues; (ii) in vitro HTS platforms of artificial tissue models to identify excipients (e.g., therapeutic-enhancing molecules that, for example, facilitate drug absorption and/or solubility and thus increase the permeability of cellular barriers to specific drugs) in normal and/or diseased tissues; (iii) in vitro HTS platforms of artificial tissue models to discover co-carriers or co-transporters of specific drugs through cellular barriers in normal and/or diseased tissues; (iv) in vitro HTS platforms of artificial tissue models to discover drug delivery systems (e.g., nano-carriers, polymers, vesicles, nano-constructs, etc.) through cellular barriers in normal and/or diseased tissues; (v) in vitro HTS platforms of artificial tissue models as surrogates for diseases (including cancer) of the skin, lung, gastrointestinal tract, endocrine/exocrine gland, capillaries and so forth to discover relevant therapeutic molecules; (vi) in vitro HTS platforms of artificial tissue models as surrogates for tissue regeneration and/or wound healing of the skin, lung, gastrointestinal tract, capillaries and so forth to discover relevant therapeutic molecules; and (vii) in vitro HTS platforms of artificial tissue models (skin, lung, esophageal, etc.) for HTS of carcinogenic molecules.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter, which is limited only by the claims which follow.

The invention claimed is:

1. A magnetically-enabled transwell system, comprising:
a cell culture vessel including at least a first chamber and a second chamber, at least one magnetic particle embedded in an extracellular matrix being disposed in the first chamber,
wherein the extracellular matrix comprises at least one cell embedded within or coating the surface of the extracellular matrix;
a perfusion mechanism including at least one elongate tubular body, each elongate tubular body defining an elongate perfusion channel having a proximal end located in the first chamber and a distal end configured for fluid communication with the second chamber, each elongate tubular body comprising at least one magnetic element which immobilizes the at least one magnetic particle embedded in the extracellular matrix such that the proximal end of the elongate perfusion channel is in fluid communication with a basolateral space of the extracellular matrix,
wherein the perfusion mechanism is configured to operate to at least one of:
infuse a medium fluid from the second chamber through at least one elongate perfusion channel into the basolateral space of at least one immobilized extracellular matrix; and
effuse a waste fluid from the basolateral space of at least one immobilized extracellular matrix through at least one elongate perfusion channel into the second chamber.

2. The system of claim 1, wherein the at least one magnetic element comprises a ferromagnetic material.

3. The system of claim 1, wherein the at least one magnetic element is the elongate tubular body itself, substantially composed of a ferromagnetic material.

4. The system of claim 1, wherein the at least one magnetic element is at least one of incorporated in and attached to the elongate tubular body at a position located at least one of along the elongate perfusion channel defined by the elongate tubular body and substantially near the distal end of the elongate perfusion channel defined by the elongate tubular body.

5. The system of claim 4, wherein the at least one magnetic element is a ring positioned to surround the elongate tubular body substantially near the distal end of the elongate perfusion channel.

6. The system of claim 1, wherein the at least one magnetic particle embedded in an extracellular matrix is at least partially coated with at least one of endothelial cells, epithelial cells, and an acellular material.

7. The system of claim 6, wherein the endothelial cells are of at least one of vascular origin and lymphatic origin.

8. The system of claim 6, wherein the epithelial cells are of at least one of skin origin, lung origin, upper respiratory tract origin, kidney origin, genitourinary origin, gastrointestinal origin, endocrine origin, and exocrine origin.

9. The system of claim 6, wherein the epithelial cells are derived from at least one of an eye or its components and an ear or its components.

10. The system of claim 6, wherein the acellular material is at least one of an organic material and an inorganic material.

11. The system of claim 1, wherein the perfusion mechanism is configured to infuse medium fluid from the second chamber through at least one elongate perfusion channel into the basolateral space of at least one extracellular matrix by at least one of:
capillary fluid movement;
communicating vessels;
a differential atmospheric pressure between the first chamber and the second chamber; and
a differential hydrostatic pressure between the first chamber and the second chamber.

12. The system of claim 1, wherein the medium fluid is a cell growth medium.

13. The system of claim 1, wherein the system is configured to simulate at least one of a perfused air-liquid interface and a perfused liquid-liquid interface.

14. The system of claim 1, wherein the perfusion mechanism is configured to effuse waste fluid from the basolateral space of at least one extracellular matrix through at least one elongate perfusion channel into the second chamber by at least one of:
diffusion;
gravity;
periodical creation of negative hydrostatic pressure in the second chamber;
periodical creation of positive hydrostatic pressure in the first chamber;
periodical creation of negative atmospheric pressure in the second chamber; and
periodical creation of positive atmospheric pressure in the first chamber.

15. The system of claim 1, wherein the at least one cell is viable more than at least one of 1 day, 2 days, 3 days, 4 days, 5 days, and 6 days.

16. The system of claim 1, wherein the at least one cell is viable more than at least one of 1 week, 2 weeks, 3 weeks, 4 weeks, 5 weeks, 6 weeks, and 7 weeks.

17. The system of claim 1, wherein the at least one cell is viable more than at least one of 2 months, 3 months, 4 months, 5 months, 6 months, and 1 year.

18. A method for immobilizing and supplying perfusion to at least one cell embedded within or coating the surface of an extracellular matrix comprising at least one embedded magnetic particle, the method comprising:
providing a magnetically-enabled transwell system comprising:
a cell culture vessel including at least a first chamber and a second chamber, at least one cell embedded within or coating the surface of an extracellular matrix comprising at least one embedded magnetic particle being disposed in the first chamber;
a perfusion mechanism including at least a first elongate tubular body, the first elongate tubular body defining a first elongate perfusion channel having a proximal end located in the first chamber and a distal end configured for fluid communication with the second chamber, the first elongate tubular body comprising at least a first magnetic element which immobilizes the extracellular matrix comprising at least one embedded magnetic particle;
immobilizing the at least one embedded magnetic particle with a magnetic pull force of at least the first magnetic element of at least the first elongate tubular body such that the proximal end of at least the first elongate perfusion channel is in fluid communication with a basolateral space of the immobilized extracellular matrix;

operating the perfusion mechanism to at least one of:
- infuse a medium fluid from the second chamber through the first elongate perfusion channel into the basolateral space of the immobilized extracellular matrix; and
- effuse a waste fluid from the basolateral space of the immobilized extracellular matrix through the first elongate perfusion channel into the second chamber.

19. The method of claim 18, further comprising a step of at least partially coating the immobilized extracellular matrix with at least one of endothelial cells, epithelial cells, and an acellular material.

20. The method of claim 18, further comprising a step of simulating at least one of a perfused air-liquid interface and a perfused interface.

\* \* \* \* \*

UNITED STATES PATENT AND TRADEMARK OFFICE
CERTIFICATE OF CORRECTION

PATENT NO. : 10,221,381 B2
APPLICATION NO. : 15/320716
DATED : March 5, 2019
INVENTOR(S) : Eugen Dhimolea et al.

It is certified that error appears in the above-identified patent and that said Letters Patent is hereby corrected as shown below:

In the Claims

Column 23, Line number 18, Claim number 20:
"a perfused interface."
Should read:
-- a perfused liquid-liquid interface. --

Signed and Sealed this
Twenty-third Day of April, 2019

Andrei Iancu
*Director of the United States Patent and Trademark Office*